United States Patent [19]

Schachar

[11] 4,127,903

[45] Dec. 5, 1978

[54] HORIZONTALLY MOUNTED INTRAOCULAR LENS AND THE METHOD OF IMPLANTATION THEREOF

[76] Inventor: Ronald A. Schachar, 213 N. Barrett, Denison, Tex. 75020

[21] Appl. No.: 765,385

[22] Filed: Feb. 3, 1977

[51] Int. Cl.² .......................... A61F 1/16; A61F 1/24
[52] U.S. Cl. ............................................................. 3/13
[58] Field of Search ........................................ 3/13, 1

[56] References Cited

U.S. PATENT DOCUMENTS 3,906,551 9/1975 Otter ............................................. 3/13

OTHER PUBLICATIONS

"A Lens for All Seasons" (book) by J. L. Tennant, pp. 13-21, 37, 46-47, Aug. 1976.
Proceedings of the Royal Society of Medicine, vol. 58, Sep. 1965, pp. 729-731, The Mark VI, Mark VII and Mark VIII Choyce Anterior Chamber Implants by Peter Choyce.
"Four Years Experience with Binkhorst Lens Implantation" by A. T. M. van Balen, American Journal of Ophthalmology, vol. 75, No. 4, May 1973, pp. 755-763.
"Technique of Phacoemulsification of Lens Implantation" by R. P. Krats, American Intra-Ocular Implant Society Journal, vol. 2, No. 1, Oct. 1976, pp. 15-16.

Primary Examiner—Ronald L. Frinks
Attorney, Agent, or Firm—Richards, Harris & Medlock

[57] ABSTRACT

An intraocular lens which may be mounted to the iris of a human eye. Two open-ended loops are attached to opposite peripheral regions of the lens and extend radially outwardly therefrom. Two pins are attached at one end to the optic lens and extend at least to the end of one of the loops. Utilizing the loops and pins, the lens may be implanted in a human eye with the pins disposed generally horizontally and through apertures in the mid region of the iris to provide significant medical advantages.

10 Claims, 5 Drawing Figures

HORIZONTALLY MOUNTED INTRAOCULAR LENS AND THE METHOD OF IMPLANTATION THEREOF

FIELD OF THE INVENTION

This invention relates to intraocular lenses, and more particularly relates to intraocular lenses which may be attached to the iris of the human eye.

THE PRIOR ART

Intraocular lenses have been heretofore successfully implanted in human eyes. For example, anterior chamber lenses have been implanted directly behind the cornea, but such a lens is sometimes considered undesirable in that it is positioned very close to the cornea and in some cases may result in traumatization of the endothelium. In order to minimize the problems of anterior chamber lenses, various iris-clip and iridocapsular lenses have been developed. For example, a lens known as the Binkhorst iris-clip lens comprises a plastic lens having four wire loops which are sutured to the iris. Such suturing is undesirable in that the sutures require special implantation techniques and in some cases may be torn loose. Moreover, the Binkhorst lens may become dislocated if the eye of the patient is dilated.

Other types of Binkhorst lenses have been developed utilizing only two loops, but such lenses require extracapsular extraction techniques, thereby requiring locking of the intraocular lens within the capsule of the crystalline lens. The locking of the two loop Binkhorst lens requires inflammation of the eye, which is often considered undesirable and which may result in a higher incidence of disease such as glaucoma or the like.

It has also been heretofore known to utilize one or more loops on an intraocular lens in combination with a single pin which is vertically placed in the top portion of the eye in order to affix the lens on the iris. However, such vertically mounted single pin devices leave a bottom loop which can dislocate. Moreover, inasmuch as the muscles and blood vessels of the iris extend radially around the iris, such vertical mounting does not obtain good support from the fibrous structure of the iris. Such vertically placed pins lens thus tend to move downwardly parallel to the iris muscle and blood vessel structure, due to the weight of the lens.

A need has thus arisen for an iris-clip intraocular lens which can be implanted in the eye in a manner to take advantage of the maximum fibrous support which may be provided by the iris. Additionally, a need has arisen for an iris-clip lens which is not subject to dislocation, but which enables the patient's eyes to be dilated and allows the iris to move freely relative to the lens.

SUMMARY OF THE INVENTION

In accordance with the present invention, an intraocular lens includes an optic lens dimensioned to be affixed to the iris of an eye. Two open-ended loops are attached at the ends thereof to the peripheral region of the optic lens. The loops extend radially outwardly from opposite sides of the optic lens. Two pins are each attached at one end to the optic lens and extend at least to the end of one of the loops.

In accordance with another aspect of the invention, an intraocular lens includes an optic lens dimensioned to be implanted in an eye. Two elongated rod members are formed into loops, the loops disposed on opposite sides of the optic lens and extending radially outwardly from the optic lens in opposite directions. The loops are attached at the ends of the rod members to peripheral regions of the optic lens. Two flexible pin members are each attached at one end to the optic lens between the ends of one of the rod members. Each pin member has a length at least as great as the length of one of the loops, such that the optic lens may be implanted in the eye with the pin members horizontally extending through the iris and clipped behind the loops.

In accordance with another aspect of the invention, a method of attaching an artificial optic lens having opposed loops and flexible pins to an iris includes the steps of forming a corneal incision in an eyeball. First and second apertures are then formed through the mid-iris of the eyeball at points generally located on a horizontal line through the center of the iris. The eye lens is extracted. The loops are oriented horizontally and are disposed posterior to the iris. The flexible pins are inserted through the apertures. The outer ends of the flexible pins are clipped posteriorly to the loops to affix the optic lens to the iris. The corneal incision is then surgically sutured.

DESCRIPTION OF THE DRAWINGS

For a more complete understanding of the present invention and for other objects and advantages thereof, reference is now made to the following description, taken in conjunction with the accompanying drawings, in which.

DESCRIPTION OF THE PREFERRED EMBODIMENT

Figure 1:
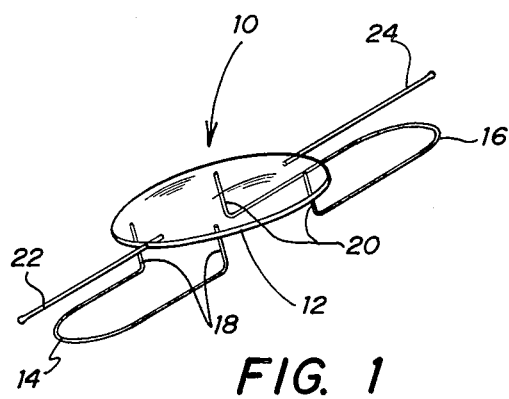
FIG. 1 is a perspective view of the present intraocular lens.

Referring to FIG. 1, the intraocular lens of the present invention is generally identified by the numeral 10 and may be seen to include a circular transparent optic lens 12. Optic lens 12 may be comprised of polymethylmethacrylate or another suitable plastic. The optic lens 12 includes an optical surface which is polished to define the desired corrected optical adjustment for a particular eye. The optic lens 12 is dimensioned to be implanted in the lens region of a human eye, and in the preferred embodiment has a diameter of approximately 5 mms.

A pair of loops 14 and 16 extend radially outwardly from opposite sides of the optic lens 12. In the preferred embodiment, The loops 14 and 16 are open-ended loops formed from bent elongated rods and each are attached at the ends thereof to the posterior surface of the optic lens 12. Loop 14 includes leg portions 18 which are attached to the optic lens 12 by fusion or the like and which extend generally perpendicularly to the lens surface. Similar leg portions 20 are formed on loop 16. The remainder of the loops 14 and 16 extend from the leg portions generally parallel to the lens surface of the optic lens 12. Loops 14 and 16 can be made of any suitable generally rigid material such as metal or plastic.

The loops can thus be formed from polymethylmethacrylate, supramid, polypropolene, titanium, platinum or platinum iridium. The loops are attached to the posterior of the optic lens 12 by fusing, adhesion or any other suitable technique. Alternatively, the loops may be integrally molded in the same mold as the lens 12 and formed from the same plastic material as the lens 12.

While it will be understood that the dimensions of loops 14 and 16 may vary for various desired applications, the distance from the peripheral edge of the optic lens 12 to the closed end of each of the loops may be 2 mm. The distance from the peripheral edge of the optic lens 12 to the connection of the leg portions to the lens surface may for example be 1 mm. The distance between the leg portions 18 may be, for example, 2 mm. In the preferred embodiment, the sides of each of the loops 14 and 16 are generally parallel to one another. The loops 14 and 16 in the preferred embodiment are disposed directly opposite one another on opposite sides of the lens 12. However, loops 14 and 16 may in some instances be slightly angled to the horizontal.

An important aspect of the present invention is the provision of pins 22 and 24 on opposite sides of the optic lens 12. Pin 22 is ideally mounted midway between the leg portions 18 of loop 14, while pin 24 is mounted midway between leg portions 20 of loop 16. For some applications, pins 22 and 24 may be offset from the midway point between the leg portions of the loops.

The pins 22 and 24 may be formed from any suitable material, but are preferably formed from supramid, polypropolene, platinum or methyl methacrylate. The pins 22 and 24 are affixed at the ends to lens 12 by any suitable technique. Alternatively, the pins 22 and 24 may be integrally molded in the same mold with the lens 12 from the same plastic as lens 12. The pins 22 and 24 extend radially outwardly from the edge of optic lens 12 past the closed ends of the loops 14 and 16. A typical length of each of the pins from the peripheral edge of the optic lens 12 to the end of the pin would be 3 mm. As will be subsequently described in the preferred embodiment, the pins 22 and 24 are sufficiently flexible to be pushed downwardly to snap in place under the generally rigid loops 14 and 16. The outer ends of the pins 22 and 24 are preferably slightly enlarged in order to tend to prevent unwanted disengagement from beneath the associated loop.

Figure 2:
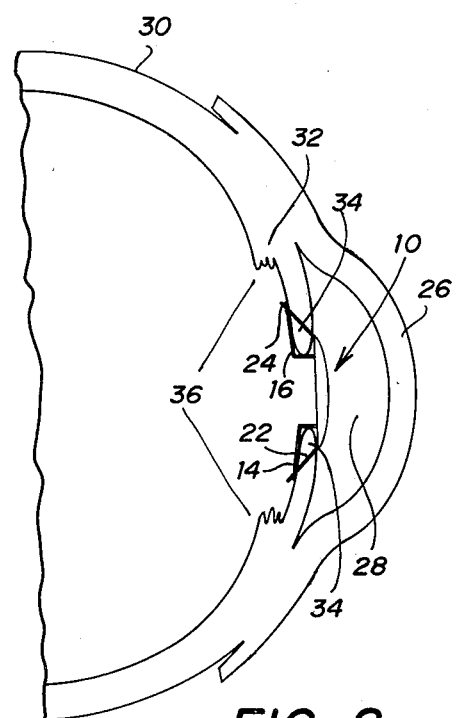
FIG. 2 is a horizontal section through a human eyeball, partially broken away, illustrating the implantation of the present lens.

Although the pins 22 and 24 are shown in FIGS. 1 and 2 as extending past the ends of loops 14 and 16, in other embodiments of the invention the pins 22 and 24 can extend only to the ends of loops 14 and 16. In such embodiments, the pins 22 and 24 may have catch portions on the ends for positively locking with the ends of loops 14 and 16. For example, the pins 22 and 24 may include curved portions for locking underneath the closed ends of loops 14 and 16.

FIG. 2 is a horizontal section illustrating the intraocular lens 10 implanted within a human eyeball. As is well known, the eyeball includes a cornea 26 which contains aqueous humor 28. The sclera 30 forms the outer housing of the eyeball. The ciliary muscle 32 comprises an annular muscle which supports the iris 34. As is known, the iris 34 comprises an annular member which may contract or expand in order to vary the light emitted into the eyeball. The ciliary muscle 32 includes suspensory ligaments 36 which normally support the lens of the eyeball behind the iris. In FIG. 2, the normal eyeball lens has been removed and the lens 10 has been implanted in its place. Lens 10 is affixed to the iris in a manner such that the iris is still free to expand or to contract. Moreover, the lens 10 is affixed or pinned to the iris in a position such that it will not normally rub on the cornea 26 and therefore corneal dystrophy does not occur with the use of the present lens.

As shown in FIG. 2, the pins 22 and 24 extend through apertures made in the mid region of the iris and clip beneath the loops 14 and 16. The lens 10 is mounted with the loops 14 and 16 in a generally horizontal plane and the pins 22 and 24 are disposed on a generally horizontal plane in order to provide advantages as will be hereinafter described.

Figure 3:
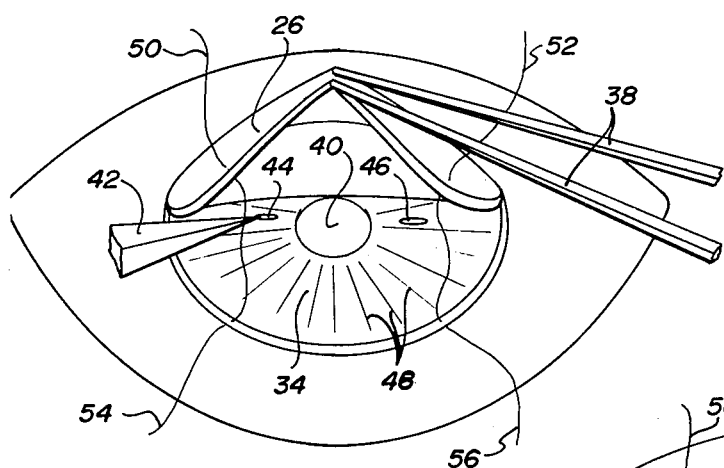
FIG. 3 is a front view of a human eyeball illustrating the initial steps of implantation of the present lens.
Figure 4:
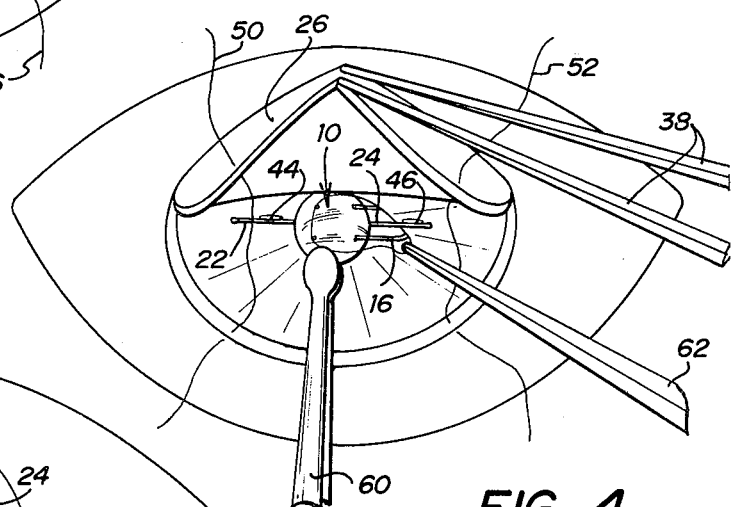
FIG. 4 is a front view of the eyeball shown in FIGURE 3, illustrating the insertion of the present lens.
Figure 5:
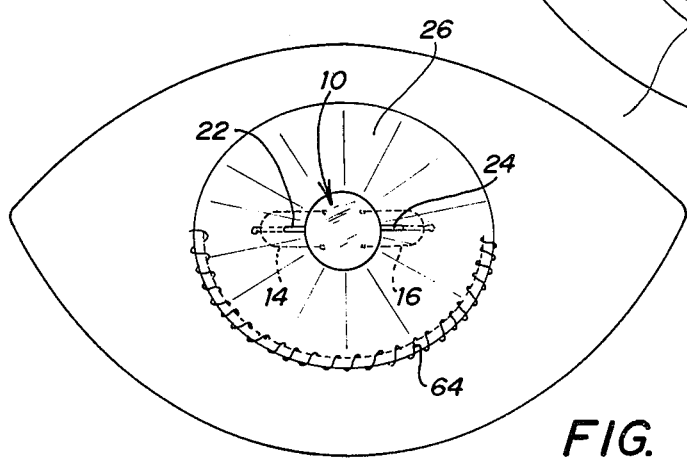
FIG. 5 is a front view of the eyeball shown in FIGURES 3 and 4 after the present lens has been implanted and after the cornea has been sutured.

FIGS. 3-5 illustrate various sequential steps of the implantation technique utilizing the present lens 10. As shown in FIG. 3, a human eye is illustrated which has a cataract. A standard cataract incision is first made with a keratome about a portion of the periphery of the cornea. A clear corneal incision is preferred, although a limbal-based or a fornix-based flap incision may be alternatively made. A 180° incision is preferred, although a lesser incision of 150° may alternatively be formed. After the incision is made about the periphery of the cornea, as shown in FIG. 3, the cornea 26 is lifted up by forceps members 38 to expose the iris 34 and the human lens 40.

Mid-iris iridotomies are then performed on opposite sides of the lens at points spaced along a horizontal line centered at the lens. The iridotomies are performed by any suitable technique, such as by puncturing with a Vannas scissors 42. The mid-iris iridotomies 44 and 46 comprise apertures formed through the iris in order to enable clipping of the intraocular lens 10 in a horizontal position as will be subsequently described.

The iris includes a concentric sphincter muscle at the pupillary margin, with the remainder of the iris including blood vessels and dilator muscle constructed in generally linear radial fashion as indicated somewhat diagrammatically by the lines 48 in FIG. 3.

If the iridotomies are formed vertically in the iris one above the other and an intraocular lens affixed therethrough, the weight of the lens would tend to be directed parallel to the muscle and blood vessel structure of the iris. The lens would tend, in some cases, to slowly move downwardly and in some cases tear the sphincter muscle of the iris, therefore totally dislocating the lens.

With the present invention, the iridotomy apertures 44 and 46 are disposed at the 180° meridian location illustrated. Thus the weight of the lens 10 is directed generally perpendicularly to the radial blood vessel and dilator muscle of the iris. Due to this perpendicular orientation, the dilator muscle is able to withstand the weight of the lens and downward movement of the lens is generally eliminated, thereby eliminating tearing of the sphincter muscle and eliminating lens dislocation.

A standard peripheral iridotomy or iridectomy is performed at the 11 o'clock or 12 o'clock position in the iris in the standard manner. As is known, this standard peripheral iridotomy or iridectomy is provided to prevent later complications by allowing some drainage of the aqueous humor of the eye.

The next step of the technique is the placement of two 8-0 black silk sutures 50 and 52 through the cornea 26 and also through scleral wounds at locations 54 and 56. This enables the cornea to be initally secured after the lens 10 is implanted. In the next step, the damaged or cataractous lens 40 is extracted either intracapsularly or extracapsularly. In the preferred embodiment, intracapsular removal of the lens is preferred to avoid post operative inflammation. The intracapsular removal will conventionally be accomplished with a cryoprobe in the known manner.

Referring to FIG. 4, the intraocular lens 10 is then inserted in the area previously occupied by the human lens 40. As shown in FIG. 4, the lens 10 is held by intraocular lens forceps 60 and the loop 16 is placed posteriorly to the iris at the three o'clock position. Microscopic angled ties 62 may be utilized in this procedure to assist in moving the iris. The pin 24 is placed in front of the iris. The end of the pin 24 is then inserted through the aperture 46 in the iris and pushed downwardly in order to clip under the loop 16 in the manner shown in FIG. 2. Similarly, utilizing a microscopic angled tie 62, the loop 14 is placed posterior to the iris. The pin 22 is then inserted through the aperture 44 and is clipped behind the loop 14. At this stage, the lens 10 is affixed to the iris and the weight of the lens is directed generally perpendicularly to the radial structure of the iris muscles, thereby preventing tearing of the iris and providing a secure iris attachment of the lens.

The two 8-0 black silk sutures 50 and 52 are then pulled together in order to place the cornea 26 in its normal position. The sutures are tied and air is then placed in the anterior chamber of the eye, maintaining the lens 10 a substantial distance from the corneal endothelium. The corneal wound is then closed in the conventional manner with the use of sutures 64, as shown in FIG. 5. Although it will be understood that various types of sutures can be utilized, in the preferred embodiment of the invention a 10-0 running suture is utilized. The air is then partially removed from the anterior chamber and the anterior chamber is reformed with balanced salt solution. Upon healing, the sutures may be removed and the eye operates in a substantially normal manner, with the artificial lens 10 taking the place of the normal eyeball lens.

With the use of the present technique, the basic iris structure is utilized for secure fixation and there is little chance for movement of the optic lens. There are no pupillary constrictive agents needed at the time of surgery or post operatively. With the present invention, the iris can be dilated immediately, allowing for excellent retinal examination and prevention of posterior synechia. The present lens sits back at the iris diaphragm from the corneal endothelium, thereby preventing damage to the cornea. Either the extracapsular or intracapsular technique can be performed with the invention, and no special suturing techniques are required.

The present technique does not require suturing of the lens to the iris, thereby eliminating problems with tearing loose of sutures or special implantation surgical techniques. The present lens implantation also eliminates dislocation of the lens upon dilation of the iris.

Whereas the present invention has been described with respect to specific embodiments thereof, it will be understood that various changes and modifications will be suggested to one skilled in the art, and it is intended to encompass such changes and modifications as fall within the scope of the appended claims.

What is claimed is:

1. An intraocular lens comprising:
   an optic lens dimensioned to be implanted in the anterior chamber of an eye and having a constant radius less than the distance from the center of the lens portion of the eye to the mid region of the iris of the eye,
   a pair of elongated rod members each formed into a loop, said loops disposed on opposite sides of said optic lens and extending radially outwardly from said optic lens in opposite directions and dimensioned in radial length to extend from the edge of the pupillary margin of the iris portion of the eye slightly past the mid region of the eye iris, said loops attached at the ends of said rod members to peripheral regions of said optic lens, and
   a pair of pin members each attached at one end to said optic lens between the ends of one of said rod members, each pin member having a length at least as great as the length of one of said loops and further having a length such that said optic lens may be implanted in the lens area of the anterior chamber of the eye with said pin members substantially horizontally extending through apertures formed through the mid region of the iris and clipped behind said loops at a position past the mid region of the iris.

2. The intraocular lens of claim 1 wherein said loops each include leg portions which extend generally perpendicularly to the lens surface and further include end portions which extend generally parallel to the lens surface.

3. The intraocular lens of claim 1 wherein the sides of said loops are generally parallel to one another.

4. The intraocular lens of claim 1 wherein said pins are formed from flexible plastic material.

5. The intraocular lens of claim 1 wherein said loops are formed from metal.

6. The intraocular lens of claim 1 wherein said loops are formed from plastic material.

7. The method of attaching an artificial optic lens having opposed loops and flexible pins to an iris comprising:
   forming a corneal incision in an eyeball,
   forming first and second apertures through the mid-iris of the eyeball between the periphery of the iris and the pupillary margin of the iris at points generally located on a horizontal line through the center of the iris,
   extracting the eye lens,
   orienting the loops horizontally,
   disposing each of the loops posterior to the iris,
   inserting the flexible pins through said apertures in the mid-iris,
   clipping the outer ends of the flexible pins posterior to the loops at a position past the mid-iris to affix the optic lens to the iris such that the weight of the optic lens is primarily perpendicular to and is borne by the radial muscle structure of the iris, and
   surgically suturing the cornal incision.

8. The method of claim 7 wherein said corneal incision is made in at least a 150° arc.

9. The method of claim 7 wherein the eye lens is extracted intracapsularly.

10. The method of claim 7 wherein air is placed in the anterior chamber of the eye to maintain the optic lens away from the corneal endothelium before the corneal incision is sutured.

* * * * *